(12) United States Patent
Mauch et al.

(10) Patent No.: US 10,220,201 B2
(45) Date of Patent: Mar. 5, 2019

(54) INTEGRITY EVALUATION SYSTEM IN AN IMPLANTABLE HEARING PROSTHESIS

(71) Applicant: Cochlear Limited, Macquarie University, NSW (AU)

(72) Inventors: Herbert Mauch, Grenzach-Wyhlen (DE); Peter Seligman, Essendon (AU); Barry Nevison, Tonbridge Kent (GB); Paul Carter, West Pennant Hills (AU)

(73) Assignee: Cochlear Limited, Macquarie University (AU)

( * ) Notice: Subject to any disclaimer, the term of this patent is extended or adjusted under 35 U.S.C. 154(b) by 35 days.

(21) Appl. No.: 15/204,139

(22) Filed: Jul. 7, 2016

(65) Prior Publication Data

US 2016/0310738 A1 Oct. 27, 2016

Related U.S. Application Data

(63) Continuation of application No. 13/114,733, filed on May 24, 2011.

(51) Int. Cl.
*A61N 1/36* (2006.01)
*A61N 1/05* (2006.01)
*H04R 25/00* (2006.01)
*A61N 1/08* (2006.01)

(52) U.S. Cl.
CPC ............ *A61N 1/0541* (2013.01); *A61N 1/08* (2013.01); *A61N 1/36036* (2017.08); *H04R 25/305* (2013.01); *H04R 25/554* (2013.01); *A61N 2001/083* (2013.01); *H04R 2225/67* (2013.01)

(58) Field of Classification Search
CPC .... A61N 1/0541; A61N 1/36032; A61N 1/08; A61N 1/36
See application file for complete search history.

(56) References Cited

U.S. PATENT DOCUMENTS

| | | | |
|---|---|---|---|
| 4,532,930 A | 8/1985 | Crosby et al. |
| 5,569,307 A | 10/1996 | Schulman et al. |
| 6,068,590 A | 5/2000 | Brisken |
| 6,317,633 B1 | 11/2001 | Jorgenson et al. |
| 6,387,048 B1 | 5/2002 | Schulman et al. |
| 6,993,384 B2 | 1/2006 | Bradley et al. |

(Continued)

FOREIGN PATENT DOCUMENTS

| | | |
|---|---|---|
| CN | 101124849 A | 2/2008 |
| WO | 9966982 A1 | 12/1999 |

(Continued)

OTHER PUBLICATIONS

European Office Action dated Dec. 2, 2015 in corresponding European Application No. 12788764A, pp. 1-4.

(Continued)

*Primary Examiner* — Michael D Abreu
(74) *Attorney, Agent, or Firm* — Edell, Shapiro & Finnan, LLC (57) ABSTRACT

An implantable hearing prosthesis, comprising an integrated integrity system. The integrity system is configured to measure one or more electrical characteristics of at least one component of the prosthesis, to evaluate the integrity of the prosthesis based on the measurements, and to perform at least one diagnostic operation based on the evaluation.

23 Claims, 5 Drawing Sheets

(56) References Cited

U.S. PATENT DOCUMENTS

| | | |
|---|---|---|
| 9,597,503 B2* | 3/2017 | Risi .................... A61N 1/36032 |
| 2004/0167586 A1 | 8/2004 | Overstreet |
| 2005/0008177 A1 | 1/2005 | Ibrahim |
| 2006/0107148 A1 | 5/2006 | Ginggen et al. |
| 2008/0125833 A1* | 5/2008 | Bradley ............... A61N 1/0551 607/60 |
| 2009/0024189 A1* | 1/2009 | Lee .................... A61N 1/36017 607/66 |
| 2009/0118797 A1* | 5/2009 | Kliger ................ A61N 1/36007 607/62 |
| 2011/0029041 A1 | 2/2011 | Wiskerke |
| 2011/0087085 A1* | 4/2011 | Tsampazis ............. A61B 5/053 600/379 |
| 2011/0125217 A1* | 5/2011 | Carter ................ A61N 1/36032 607/56 |

FOREIGN PATENT DOCUMENTS

| | | |
|---|---|---|
| WO | 2009026625 A1 | 3/2009 |
| WO | 2010034080 A1 | 4/2010 |

OTHER PUBLICATIONS

Chinese Office Action w/ Search Report dated Dec. 29, 2015 in corresponding Chinese Application No. 201280036625.2, pp. 1-15.
European Search Report for European Application No. 12788764.4 dated Oct. 10, 2014.
International Search Report and Written Opinion for International Application No. PCT/IB2012/052590 dated Jan. 17, 2013 (9 pages).

* cited by examiner

INTEGRITY EVALUATION SYSTEM IN AN IMPLANTABLE HEARING PROSTHESIS

CROSS-REFERENCE TO RELATED APPLICATIONS

This application is a continuation of U.S. patent application Ser. No. 13/114,733, filed May 24, 2011, the content of which is incorporated herein by reference.

BACKGROUND

Field of the Invention

The present invention relates to implantable hearing prosthesis, and more particularly, to an integrity testing system in an implantable hearing prosthesis.

Related Art

Implantable hearing prostheses include implantable hearing aids, cochlear implants, optically stimulating implants, middle ear stimulators, bone conduction devices, brain stem implants, direct acoustic cochlear stimulators, electro-acoustic devices and other devices providing acoustic, mechanical, optical, and/or electrical stimulation to an element of a recipient's ear. Such devices are subject to failure or malfunctions due to, for example, manufacturing defects, degradation of materials over time or changes in the recipient's inner-ear function. If an issue is reported with a conventional implantable hearing prosthesis, an appointment is required with a health care professional, referred to herein as clinician, at a clinic where a number of tests are carried out to test the integrity of the prosthesis, and to determine the source of the failure. These tests are performed using specialist integrity testing equipment, and are performed in a reactive manner. That is, such testing is only performed after a recipient or user has indicated that there may be a problem with the hearing prosthesis, such as a decrease in hearing performance or other non-auditory symptoms that reduce device effectiveness.

The clinician who performs such testing is generally a specialist who is trained to use specialized integrity testing equipment. As such, the testing is generally expensive and time-consuming procedure for all involved. Furthermore, because device problems may be intermittent, the test results may be inconclusive, provide a false positive (false conclusion that the device is working correctly), and/or require subsequent additional follow-up testing to determine the nature of the problem.

SUMMARY

In one aspect of the present invention, an implantable hearing prosthesis is provided. The prosthesis comprises: an integrated integrity system configured to measure one or more electrical characteristics of at least one component of the prosthesis, to evaluate the integrity of the prosthesis based on the measurements, and to perform at least one diagnostic operation based on the evaluation.

In another embodiment of the present invention, a method for evaluating the integrity of an implantable hearing prosthesis is provided. The method comprises: measuring one or more electrical characteristics of at least one component of the prosthesis; determining, based on the measurements, if there is error in the operation of the prosthesis; and performing at least one diagnostic operation to determine whether there is an error in the operation of the prosthesis.

In a still other embodiment of the present invention, an implantable hearing prosthesis is provided. The prosthesis comprises: means for measuring one or more electrical characteristics of at least one component of the prosthesis; means for determining, based on the measurements, if there is an error in the operation of the prosthesis; and means for performing at least one diagnostic operation to determine whether there is an error in the operation of the prosthesis.

BRIEF DESCRIPTION OF THE DRAWINGS

Embodiments of the present invention will be described with reference to the drawings in which.

DETAILED DESCRIPTION

Embodiments of the present invention are generally directed to an implantable hearing prosthesis comprising an integrated system that is configured to evaluate the integrity or operational performance of the prosthesis. This integrated system, referred to herein as an integrity evaluation system or simply integrity system, is configured to measure one or more electrical characteristics of a component of the prosthesis. The system evaluates the integrity of the prosthesis based on these measurements, and performs at least one diagnostic operation based on the evaluation. In one embodiment, the diagnostic operation is a notification of an error identified during the evaluation. In another embodiment, the diagnostic operation is an adjustment of one or more of settings in the device to correct an error identified during the evaluation.

The integrity system uses one or more of a number of different measurements to evaluate whether the prosthesis is operating as desired. In particular, the voltage of the power supply, the electrode voltage and/or the electrode impedance, is measured and used to evaluate the operational performance.

As noted above, implantable hearing prostheses include implantable hearing aids, cochlear implants, optically stimulating implants, middle ear stimulators, bone conduction devices, brain stem implants, direct acoustic cochlear stimulators, electro-acoustic devices and other devices providing acoustic, mechanical, optical, and/or electrical stimulation to an element of a recipient's ear. Such prostheses may experience a number of failures including, but not limited to, electrode damage, malfunctioning implantable electronics, such as intermittent operation resulting from radio frequency link insufficiencies, or other conditions resulting in an unstable power supply voltage.

Embodiments of the present invention are described herein with reference to a specific implantable hearing prosthesis, namely a cochlear implant comprising an implantable component and an external component. It would be appreciated that embodiments of the present invention are not limited to this particular type of prosthesis and may be implemented in other implantable hearing prosthesis.

Figure 1:
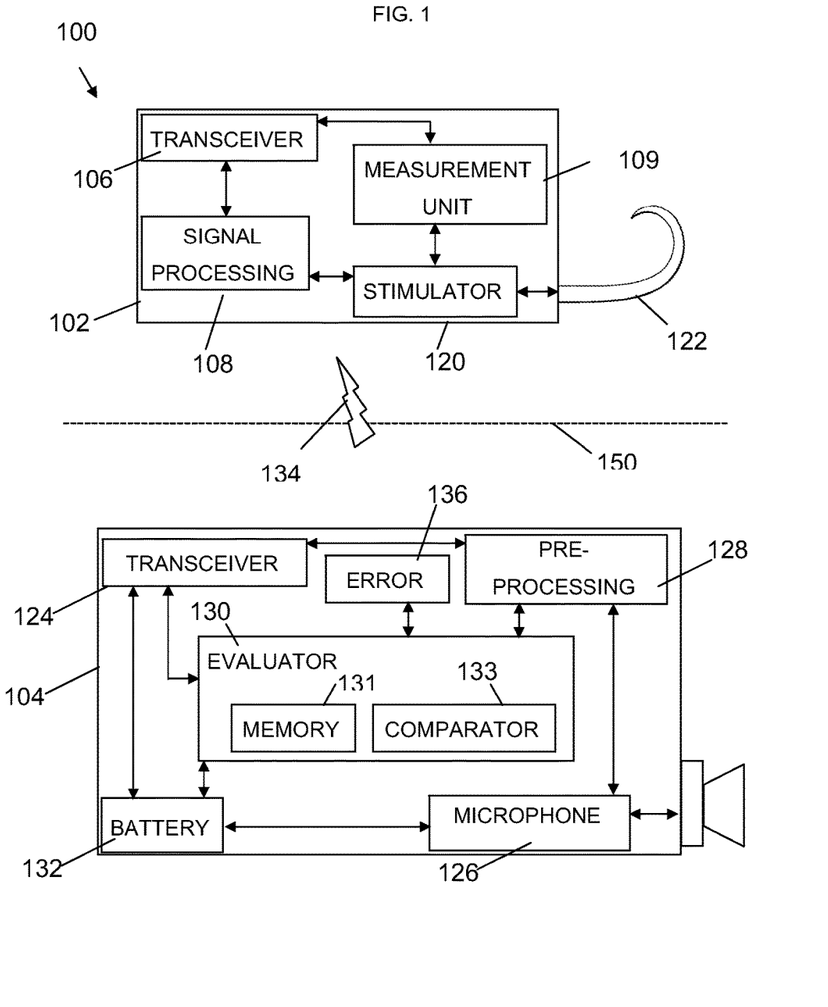
FIG. 1 is a schematic block diagram illustrating an implantable hearing prosthesis having an integrated integrity system therein, in accordance with embodiments of the present invention.

FIG. 1 is a schematic block diagram of a cochlear implant 100 in accordance with embodiments of the present invention. As shown, cochlear implant 100 comprises an implantable component comprising a main module 102 and an electrode array 122. Main module 102 comprises a transceiver 106, a signal processing unit 108, an integrity measurement unit 109, and a stimulator 120.

Cochlear implant 100 further comprises an external component 104. External component 104 includes a transceiver 124 that transfers power and/or data to transceiver 106 via an inductive radio frequency (RF) link 134, a microphone 126, pre-processing unit 128, and a battery 132. External component 104 also includes an evaluator 130 that, along with measurement unit 109, form an integrity system. Evaluator 130 is configured to process calculations made by measurement unit 109, and/or store the processed values or measurements in memory 131. Evaluator 130 further includes a comparator 133 that compares measured/processed values stored in memory with pre-determined thresholds that are also stored in memory. Such pre-determined thresholds may be being either fixed values or values dependent on results of calculations.

As noted above, external component 104 includes a pre-processing unit 128. Pre-processing unit 128 processes the output of microphone 126 that is positioned on the ear of the implant recipient. The coded signals generated by pre-processing unit 128 are provided to the transceiver 124 for transmission to transceiver 106.

The data signals received by transceiver 106 are processed by signal processing unit 108, then provided to stimulator 120. Stimulator 120 generates electrical stimulation signals for delivery to the receiver via electrodes of electrode array 122. Electrode array 122 may comprises one or more reference electrodes, extra-cochlea electrodes, or electrodes implanted in the recipient's cochlear. As such, the stimulation signals are delivered to the nerve cells in a recipient's cochlea, thereby facilitating perception of sound received by microphone 126.

As noted above, cochlear implant 100 includes an integrity system comprising measurement unit 109 and evaluator 130. The integrity system is configured to perform a number of tests to evaluate the operation of cochlear implant 100. These tests may be initiated manually or automatically. Additionally, the tests may be continuous (i.e. be continually performed during operation of the implant) or may be performed periodically.

In embodiments of the present invention, a test is initiated by evaluator 130 via communication link 134, and is performed by measurement unit 109. The results of the measurement are then sent back to evaluator 130 via communication link 134. Evaluator 130 processes the results of the tests and may then perform one or more diagnostic operations based thereon. The diagnostic operations include, for example, taking action to rectify or mitigate the identified issue, storing the results in memory 131 for later analysis, report or signal the issue in an identifiable manner to the recipient or other user, etc. In one embodiment, evaluator 130 activates an error indicating unit 136 that notifies the recipient of the issue. Error indicating unit 136 notifies the recipient of the error using, for example, a recorded announcement streamed to the recipient from memory 131, or a warning light or LED, or other audible or visual indicator.

Figure 2:
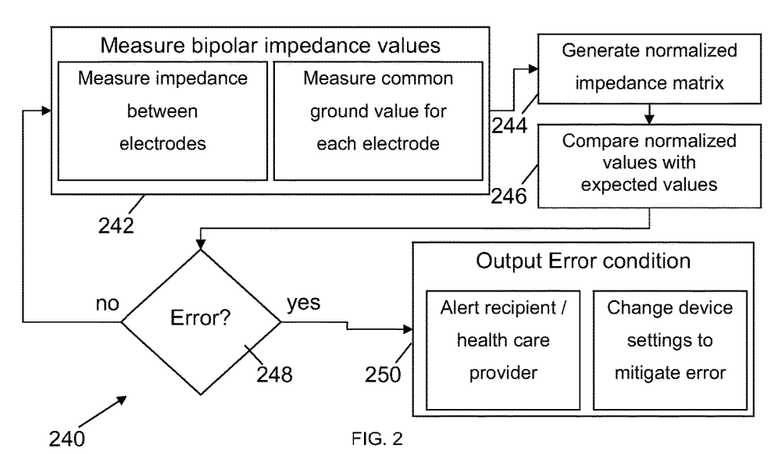
FIG. 2 illustrates a method of assessing the integrity of an implantable hearing prosthesis, in accordance with embodiments of the present invention.

FIG. 2 is a flowchart illustrating a method 240 of evaluating or assessing the integrity of an implantable hearing prosthesis, such as cochlear implant 100 of FIG. 1. The method begins at step 242 where bipolar impedance values are obtained from the electrodes of cochlear implant electrode array. As shown, step 242 includes two actions, including measuring the impedance between each of the electrodes, and then performing a common ground measurement. These measurements are described in greater detail below. Generally, the voltage between the relevant electrodes is measured at a known current, and Ohm's law is used to calculate the impedance. If the same stimulation current is used, it is possible to use voltage values instead of impedance values. By way of example, the following description of method 240 will explain the steps involved using impedance values. It should be understood, however, that voltage values can be used in the same manner.

Once the bipolar impedance values have been obtained, a normalized impedance matrix is generated at step 244. One exemplary method for generating a normalized impedance matrix is described in detail below. Next, at step 246, the normalized impedance matrix is compared with expected values to determine whether the integrity of the device is as expected, that is, whether an issue has been detected. It would be appreciated that this comparison step does not necessarily involve a direct comparison of two values, but rather may involve calculations based on the normalized impedance values. For example, comparison of one electrode's impedance or voltage values to the average values for all other electrodes may provide an indication of an issue.

Based on the results of the comparison at step 246, an issue decision is made at step 248. If no issue is indicated, then method 240 returns to step 242 to measure the impedance values, and the method is repeated. If an issue is detected, a diagnostic operations 250 is performed. The type of diagnostic operation 250 provided may depend on different factors, such as what issue is detected. As noted above, one output is to alert the recipient that the integrity system has detected an issue. Alternatively or additionally, other diagnostic operations include alerting a health care provider or storing an alert for an appropriate time, such as at the next visit to the health care provider. Additionally, the diagnostic operation may include taking corrective action to alter settings of the cochlear implant so as to attempt to remedy the issue. Potential corrective actions for a cochlear implant are discussed in detail below.

A number of different types of integrity tests may be implemented by an integrity system in accordance with embodiments of the present invention. A first such test is referred to herein as a supply voltage test. The supply voltage test is used to evaluate the stability of the implant's power supply voltage (Vdd) over a period of time and under various load conditions. The load condition of the supply voltage may depend on, for example, the effective total stimulation rate, the electrode impedances, the loudness of the overall sound environment, etc. Additionally, because in certain implants the RF link 134 (FIG. 1) is used to transfer power and data from the external component 104, the main module 102 has supply voltage (Vdd) dependent on the stability of the RF link. One test involves measuring the value of Vdd over time while varying the RF power level (energy level) of the RF link, and tracking the stability of Vdd. Alternatively or additionally, the supply voltage test may measure the effective current drawn from battery 132.

As noted above, certain tests in accordance with embodiments of the present invention may be performed continuously or periodically. In one embodiment, the Vdd stability is continually or periodically tracked and stored by evaluator 130 in memory 131. This allows for monitoring of daily real life conditions, as compared with laboratory or clinic conditions. That is, the supply voltage can be monitored during stimulation as well as in specific test conditions.

In certain embodiments of the present invention, cochlear implant 100 has an alternative external or internal power source. In such embodiments, the RF link 134 may not be used for transmission of power, but monitoring of Vdd may be still be performed using other methods to determine, for example, if battery is defective or there is some other electrical fault.

Another test that may be used in embodiments of the present invention is the bipolar impedance electrode array test. In this test, measurement unit 109 measures the electrode potentials generated as a result of electrical stimulation so as to determine the impedance of the electrodes in the array. That is, the measured voltage between two or more electrodes, along with the knowledge of the current that was supplied, allows impedance to be calculated using Ohm's law.

The electrode array test detects and measures anomalous and unwanted stimulation current flow between individual electrodes of an electrode array through the use of variable bipolar impedance measurements, and a normalization calculation on the resulting impedance matrix. Alternatively, the variable bipolar voltage measurements and a normalization calculation of the resulting voltage matrix is used. The normalization allows a clear distinction of electrodes showing anomalies, as compared to electrodes that are operating according to specification. Furthermore, the normalization shows characteristic signatures for physiological/anatomical properties in the cochlea, such as ossification and scar tissue growth around the in-situ electrode array.

The exemplary electrode array test described herein refers to calculating impedance values, creating an impedance matrix and creating a normalized impedance matrix. However, it would be appreciated that voltage, current and impedance have a fixed relationship and, therefore, it is possible to generate a voltage matrix which can be used in the same manner as an impedance matrix and create a normalized voltage matrix. Therefore, the same principles as described herein may be used to create and use a normalized voltage matrix.

The creation and use of an intra-cochlear impedance matrix is described in detail below. The matrix that is created can be used to provide information on the insulation properties between the physical electrode contacts and can detect conductive bridges between individual electrodes.

In an exemplary electrode array test, evaluator 130 instructs stimulator 120 to deliver a pre-determined stimulation current over each electrode pair of electrode array 122. Measurement unit 109 performs voltage measurements for the relevant electrode pair when a stimulation current is applied. By measuring the resulting electrode voltage and the known stimulation current, the impedance for the respective electrode pair is calculated. The voltage measurements are returned to evaluator 130 via transceivers 106 and 124.

The measurement sequence contains a series of variable bipolar impedance measurements, covering all electrodes in electrode array 122. A bipolar (BP) impedance measurement measures the impedance between a pair of the electrodes.

In one illustrative implementation, electrode array 122 comprises twenty two electrodes in a line (a one dimensional array). The electrodes may be conveniently referred to as electrodes E1 to E22. The first impedance measurement is made between a first electrode E 1, which acts as an active electrode, and a second electrode E2, immediately beside the first electrode, that acts as an indifferent electrode. This is known as a BP+1 measurement it measures the impedance between an indifferent electrode (E2) that is one higher (numerically and physically), in the array than the active electrode (E1). If E2 is the active electrode and E 1 the indifferent electrode, then the impedance measurement is known as a BP−1. By further increasing the distance from the first electrode, the bipolar mode widens to BP+2, BP+3, and so forth up to the number of electrodes available on the array. Each electrode is operated as active electrode and the impedance measured against each of the other electrodes in the array, giving a matrix of measurements 22 by 22 in size, as shown below in Table 1.

TABLE 1

Matrix of variable width bipolar impedance relationships

|  |  | Indifferent Electrode | | | | | | | | | | |
| --- | --- | --- | --- | --- | --- | --- | --- | --- | --- | --- | --- | --- |
|  |  | E1 | E2 | E3 | E4 | E5 | E6 | E7 | E8 | E9 | E10 | E11 |
| Active Electrode | E1 | CG | BP+1 | BP+2 | BP+3 | BP+4 | BP+5 | BP+6 | BP+7 | BP+8 | BP+9 | BP+10 |
|  | E2 | BP−1 | CG | BP+1 | BP+2 | BP+3 | BP+4 | BP+5 | BP+6 | BP+7 | BP+8 | BP+9 |
|  | E3 | BP−2 | BP−1 | CG | BP+1 | BP+2 | BP+3 | BP+4 | BP+5 | BP+6 | BP+7 | BP+8 |
|  | E4 | BP−3 | BP−2 | BP−1 | CG | BP+1 | BP+2 | BP+3 | BP+4 | BP+5 | BP+6 | BP+7 |
|  | E5 | BP−4 | BP−3 | BP−2 | BP−1 | CG | BP+1 | BP+2 | BP+3 | BP+4 | BP+5 | BP+6 |
|  | E6 | BP−5 | BP−4 | BP−3 | BP−2 | BP−1 | CG | BP+1 | BP+2 | BP+3 | BP+4 | BP+5 |
|  | E7 | BP−6 | BP−5 | BP−4 | BP−3 | BP−2 | BP−1 | CG | BP+1 | BP+2 | BP+3 | BP+4 |
|  | E8 | BP−7 | BP−6 | BP−5 | BP−4 | BP−3 | BP−2 | BP−1 | CG | BP+1 | BP+2 | BP+3 |
|  | E9 | BP−8 | BP−7 | BP−6 | BP−5 | BP−4 | BP−3 | BP−2 | BP−1 | CG | BP+1 | BP+2 |
|  | E10 | BP−9 | BP−8 | BP−7 | BP−6 | BP−5 | BP−4 | BP−3 | BP−2 | BP−1 | CG | BP+1 |
|  | E11 | BP−10 | BP−9 | BP−8 | BP−7 | BP−6 | BP−5 | BP−4 | BP−3 | BP−2 | BP−1 | CG |
|  | E12 | BP−11 | BP−10 | BP−9 | BP−8 | BP−7 | BP−6 | BP−5 | BP−4 | BP−3 | BP−2 | BP−1 |
|  | E13 | BP−12 | BP−11 | BP−10 | BP−9 | BP−8 | BP−7 | BP−6 | BP−5 | BP−4 | BP−3 | BP−2 |
|  | E14 | BP−13 | BP−12 | BP−11 | BP−10 | BP−9 | BP−8 | BP−7 | BP−6 | BP−5 | BP−4 | BP−3 |
|  | E15 | BP−14 | BP−13 | BP−12 | BP−11 | BP−10 | BP−9 | BP−8 | BP−7 | BP−6 | BP−5 | BP−4 |
|  | E16 | BP−15 | BP−14 | BP−13 | BP−12 | BP−11 | BP−10 | BP−9 | BP−8 | BP−7 | BP−6 | BP−5 |
|  | E17 | BP−16 | BP−15 | BP−14 | BP−13 | BP−12 | BP−11 | BP−10 | BP−9 | BP−8 | BP−7 | BP−6 |

TABLE 1-continued

Matrix of variable width bipolar impedance relationships

| | E18 | BP−17 | BP−16 | BP−15 | BP−14 | BP−13 | BP−12 | BP−11 | BP−10 | BP−9 | BP−8 | BP−7 |
|---|---|---|---|---|---|---|---|---|---|---|---|---|
| | E19 | BP−18 | BP−17 | BP−16 | BP−15 | BP−14 | BP−13 | BP−12 | BP−11 | BP−10 | BP−9 | BP−8 |
| | E20 | BP−19 | BP−18 | BP−17 | BP−16 | BP−15 | BP−14 | BP−13 | BP−12 | BP−11 | BP−10 | BP−9 |
| | E21 | BP−20 | BP−19 | BP−18 | BP−17 | BP−16 | BP−15 | BP−14 | BP−13 | BP−12 | BP−11 | BP−10 |
| | E22 | BP−21 | BP−20 | BP−19 | BP−18 | BP−17 | BP−16 | BP−15 | BP−14 | BP−13 | BP−12 | BP−11 |

Indifferent Electrode

| | | E12 | E13 | E14 | E15 | E16 | E17 | E18 | E19 | E20 | E21 | E22 |
|---|---|---|---|---|---|---|---|---|---|---|---|---|
| Active Electrode | E1 | BP+11 | BP+12 | BP+13 | BP+14 | BP+15 | BP+16 | BP+17 | BP+18 | BP+19 | BP+20 | BP+21 |
| | E2 | BP+10 | BP+11 | BP+12 | BP+13 | BP+14 | BP+15 | BP+16 | BP+17 | BP+18 | BP+19 | BP+20 |
| | E3 | BP+9 | BP+10 | BP+11 | BP+12 | BP+13 | BP+14 | BP+15 | BP+16 | BP+17 | BP+18 | BP+19 |
| | E4 | BP+8 | BP+9 | BP+10 | BP+11 | BP+12 | BP+13 | BP+14 | BP+15 | BP+16 | BP+17 | BP+18 |
| | E5 | BP+7 | BP+8 | BP+9 | BP+10 | BP+11 | BP+12 | BP+13 | BP+14 | BP+15 | BP+16 | BP+17 |
| | E6 | BP+6 | BP+7 | BP+8 | BP+9 | BP+10 | BP+11 | BP+12 | BP+13 | BP+14 | BP+15 | BP+16 |
| | E7 | BP+5 | BP+6 | BP+7 | BP+8 | BP+9 | BP+10 | BP+11 | BP+12 | BP+13 | BP+14 | BP+15 |
| | E8 | BP+4 | BP+5 | BP+6 | BP+7 | BP+8 | BP+9 | BP+10 | BP+11 | BP+12 | BP+13 | BP+14 |
| | E9 | BP+3 | BP+4 | BP+5 | BP+6 | BP+7 | BP+8 | BP+9 | BP+10 | BP+11 | BP+12 | BP+13 |
| | E10 | BP+2 | BP+3 | BP+4 | BP+5 | BP+6 | BP+7 | BP+8 | BP+9 | BP+10 | BP+11 | BP+12 |
| | E11 | BP+1 | BP+2 | BP+3 | BP+4 | BP+5 | BP+6 | BP+7 | BP+8 | BP+9 | BP+10 | BP+11 |
| | E12 | CG | BP+1 | BP+2 | BP+3 | BP+4 | BP+5 | BP+6 | BP+7 | BP+8 | BP+9 | BP+10 |
| | E13 | BP−1 | CG | BP+1 | BP+2 | BP+3 | BP+4 | BP+5 | BP+6 | BP+7 | BP+8 | BP+9 |
| | E14 | BP−2 | BP−1 | CG | BP+1 | BP+2 | BP+3 | BP+4 | BP+5 | BP+6 | BP+7 | BP+8 |
| | E15 | BP−3 | BP−2 | BP−1 | CG | BP+1 | BP+2 | BP+3 | BP+4 | BP+5 | BP+6 | BP+7 |
| | E16 | BP−4 | BP−3 | BP−2 | BP−1 | CG | BP+1 | BP+2 | BP+3 | BP+4 | BP+5 | BP+6 |
| | E17 | BP−5 | BP−4 | BP−3 | BP−2 | BP−1 | CG | BP+1 | BP+2 | BP+3 | BP+4 | BP+5 |
| | E18 | BP−6 | BP−5 | BP−4 | BP−3 | BP−2 | BP−1 | CG | BP+1 | BP+2 | BP+3 | BP+4 |
| | E19 | BP−7 | BP−6 | BP−5 | BP−4 | BP−3 | BP−2 | BP−1 | CG | BP+1 | BP+2 | BP+3 |
| | E20 | BP−8 | BP−7 | BP−6 | BP−5 | BP−4 | BP−3 | BP−2 | BP−1 | CG | BP+1 | BP+2 |
| | E21 | BP−9 | BP−8 | BP−7 | BP−6 | BP−5 | BP−4 | BP−3 | BP−2 | BP−1 | CG | BP+1 |
| | E22 | BP−10 | BP−9 | BP−8 | BP−7 | BP−6 | BP−5 | BP−4 | BP−3 | BP−2 | BP−1 | CG |

The diagonal of the matrix is populated with common ground measurements for the respective electrode. Common Ground (CG) measurements measure an intra-cochlear electrode as an active electrode against all the other intra-cochlear electrodes connected together via a temporary short circuit so as to function as a collective indifferent electrode.

After acquisition and storage of the impedance measurements, the variable bipolar measurements are normalized by the use of the respective common ground impedance value for both the active and indifferent electrode of the bipolar pair. The normalized impedance $Z_{norm}$ for each Bipolar pair can calculated by the use of Equation 1:

$$Z_{norm} = \frac{Z_{BP} - Z_{CG(indifferent)}}{Z_{CG(active)}} \quad \text{Equation 1}$$

Normalized impedance

The resulting normalized impedance matrix can then be stored, in memory 131, and compared, using comparator 133, with past impedance measurements. An issue is identified if the comparison determines that the measurement deviates from the stored value by a predetermined threshold. This results in a diagnostic operation as described above.

Figure 3:
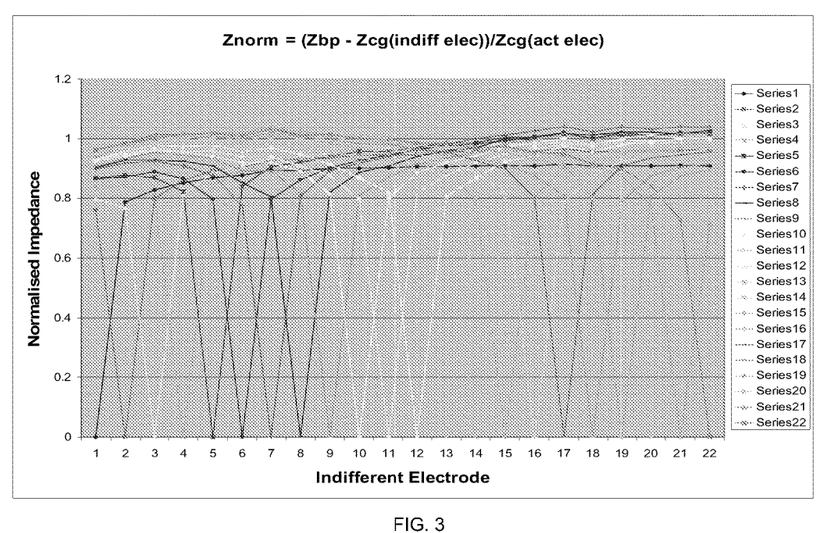
FIG. 3 are graphs of a normalized variable bi-polar impedance measurement matrix, in accordance with embodiments of the present invention.

An exemplary output response of an electrode array is shown in FIG. 3. More specifically, FIG. 3 illustrates that the normalized impedances have a value of zero when the indifferent and active electrodes are the same, increase to a value of around 0.7 to 0.8 at the direct neighboring electrode, and asymptotically reach a value of around 1 for electrode numbers more distant on either side of the active electrode.

Comparison of the normalized impedance of the electrodes can be further simplified by comparing electrodes at a common distance from other electrodes. As noted above, for a typical electrode array, the normalized impedances have a value of zero when the indifferent and active electrodes are the same. By comparing indifferent electrodes at the same distance in the array from the active electrode, a response function can be determined that again can be bounded by a pre-determined threshold to indicate whether function is within an acceptable tolerance.

Figure 4:
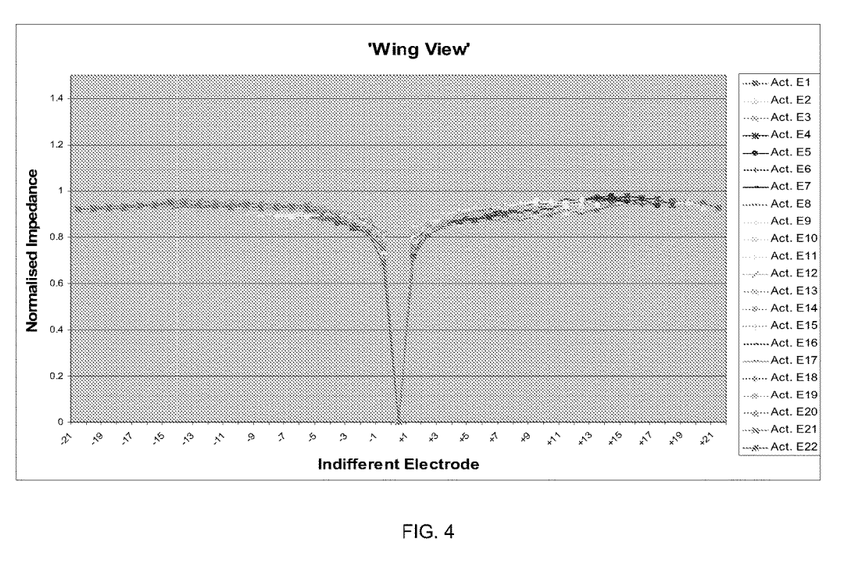
FIG. 4 are graphs of a representation of a normalized variable bi-polar impedance measurement matrix, by common distance from the active electrode, in accordance with embodiments of the present invention.

FIG. 4 is a plot of normalized impedance measurements grouped by distance from the active electrode. FIG. 4 shows that, in this example, when electrodes are compared by their distance from the active electrode, the normalized impedance measurements vary by, at most, 0.1. In this manner, evaluator 130 could, for example, determine that a normalized impedance measurement greater than 0.15 from the other normalized impedance measurements, at the same distance from the active electrode, identifies an impedance issue that requires a diagnostic operation, such as reporting to the recipient or healthcare professional in an identifiable manner.

Figure 5:
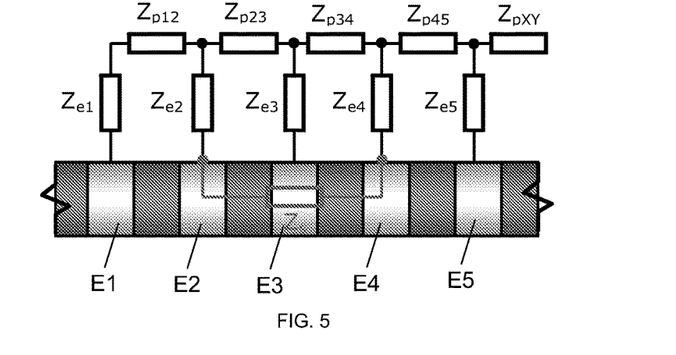
FIG. 5 illustrates a portion of an electrode array and a model of the resistance values present when insulation breakdown occurs, in accordance with embodiments of the present invention.

FIG. 5 illustrates a model showing that the electrode profiles in the normalized impedance matrix will change based on the presence of a shunt impedance between two electrodes, or due to changes in the perilymph properties in the cochlea. FIG. 5 shows only a portion of an electrode array 122 containing electrodes E1 to E5. The model divides the intracochlear impedance, which is seen by the stimulation current driven over the electrodes, into the electrode tissue impedance component ($Z_{e1}$ to $Z_{e5}$) and the perilymph impedance component ($Z_{p12}$ to $Z_{p45}$) between each electrode. In this example, a shunt impedance ($Z_s$) is present between electrodes E2 and E4. A shunt impedance, in this context, is an unintended electrical path with a particular impedance value. This could be due to, for example, the breakdown on an insulating barrier between electrodes that creates at least a partial unintended electrical path.

If the normalized impedance for an electrode pair is affected by a shunt impedance ($Z_{norm(shunt)}$), the shunt impedance $Z_s$ will be in parallel to the electrode tissue impedance between the electrode pair. This will influence both the bipolar impedance measurements between the two electrodes affected, and the common ground impedance measurement for both the active and indifferent electrode of the pair. The resulting influence on the normalized impedance can be described by Equation 2.

Normalized impedance involving shunt  Equation 2

$$Z_{norm(shunt)} = \frac{Z_{BP}||Z_s - Z_{CG(indifferent)}||Z_s}{Z_{CG(active)}||Z_s}$$

If the electrode pair in an implantable hearing device is affected by a weak shunt impedance, the shunt impedance will be large compared to the bipolar impedance over the affected electrode pair. The normalized impedance will not be affected as shown in Equation 3 and will give an expected value of 0.7 to 1, depending on the width of the bipolar mode (that is, the distance from the active electrode) for this electrode pair.

$$Z_{norm(shunt)} = Z_{norm} \Rightarrow 1 \text{ with } Z_s \geq Z_{BP}$$

Equation 3: Normalized impedance involving weak shunt

If the electrode pair in an implantable hearing device is affected by a strong shunt impedance, the shunt impedance will be equal or smaller compared to the bipolar impedance over the affected electrode pair. The normalized impedance will be affected by the shunt as shown in Equation 4 and depending on the magnitude of the shunt will tend towards a value of 0.

Normalized impedance involving strong shunt  Equation 4

$$Z_{norm(shunt)} = \frac{Z_s - Z_s}{Z_s} \Rightarrow 0$$

with $Z_s \leq Z_{BP}$

Accordingly, shunt impedances, which are representative of unintended electrical paths between electrodes, can be detected by comparison of the impedance values against expected values, as well as against corresponding values at the same distance from the active electrode.

In addition, the normalized impedance matrix can be used to identify changes in the properties of the perilymph in the cochlea, such as scar tissue growth or ossification, which would increase the perilymph impedance. This influence of the perilymph impedance on the normalized impedance can be shown in Equation 5, where the variable bipolar and common ground impedance components of the normalized impedance matrix are replaced with their electrode-tissue ($Z_e$) and perilymph impedance ($Z_p$) components. $Z_{p(n,m)}$ in Equation 5 is the perilymph impedance between a bipolar electrode pair and $Z_{p(n,x)}$ the perilymph impedance seen by a common ground measurement.

Normalized impedance based on  Equation 5 electrode-tissue and perilymph impedance $$Z_{norm} = \frac{(Z_{e(n)} + Z_{p(n,m)} + Z_{e(n)}) - (Z_{e(m)} + Z_{p(n,x)})}{Z_{e(n)} + Z_{p(n,x)}}$$

Rearranging the equation yields Equation 6.

impedance based on electrode-tissue  Equation 6 and perilymph impedance (simplified)

$$Z_{norm} = \frac{Z_{e(n)} + Z_{p(n,m)} - Z_{p(n,x)}}{Z_{e(n)} + Z_{p(n,x)}}$$

Changes in the perilymph properties of the cochlea will not generally affect the whole area of the electrode array equally. Rather, the changes will affect local areas around a group of electrodes, for example, a group of electrodes comprising the electrodes on the basal and apical sides of the electrode. The perilymph component of the bipolar electrode pair is more affected by such changes and the perilymph component seen by the common ground impedance measurement is only significantly affected if most of the indifferent electrodes would be affected. Using this simplification it can be assumed that changes in the perilymph property will increase the bipolar component as shown in Equation 7. Local increases in perilymph impedances due to, for example, scar tissue growth or ossification will yield a value for the normalized impedance of larger than one.

Influence of increased perilymph impedance  Equation 7

$$Z_{norm} = \frac{Z_{e(n)} + Z_{p(n,m)} \uparrow - Z_{p(n,x)}}{Z_{e(n)} + Z_{p(n,x)}} \geq 1$$

Figure 6:
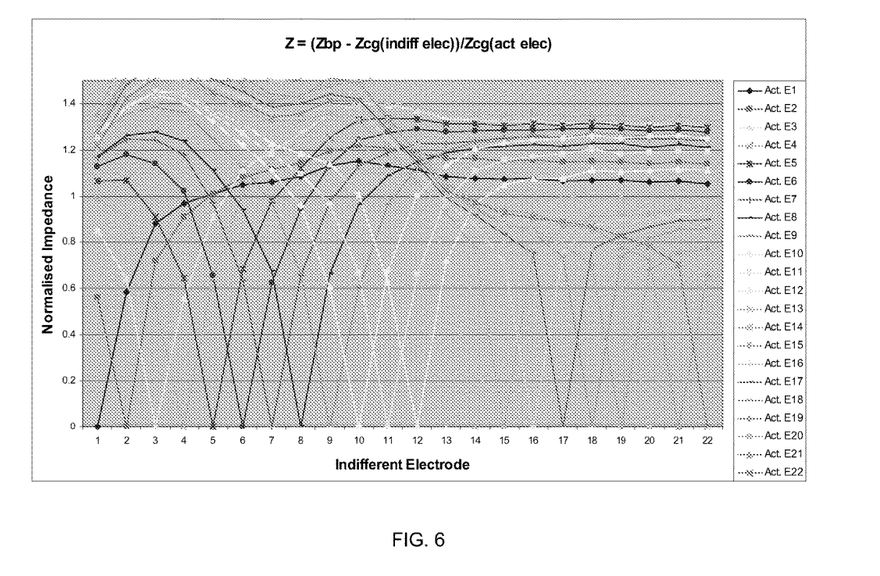
FIG. 6 graphs a normalized representation of a variable bi-polar impedance measurement matrix of a cochlea which is partially ossified, in accordance with embodiments of the present invention.

FIG. 6 is a graph showing a plot of an example of a normalized impedance matrix of an electrode array in a partially ossified cochlea. Electrodes E 1 to around E12 show an increased perilymph impedance, which is caused by, for example, scar tissue growth or ossification in this area.

Self-Correcting

Following implantation, and at subsequent times, physiological changes occur within the recipient. As such, there is a need to determine the actual performance of an electrode array and the response to stimulation provided by the array. For example, in an implantable hearing device, the response of the auditory nerve to stimulation by the electrode array is determined. Data collection for this purpose enables detection and confirmation of the normal operation of the device, and allows stimulation parameters to be optimized to suit the characteristics of the recipient. In the case of an implantable hearing device, this procedure can include determination of recipient specific parameters such as threshold levels (T levels) and maximum comfort levels (C levels) for each stimulation channel. Such data collection can be performed manually in a clinical setting by relying on subjective recipient responses, or by taking measurements directly from the cochlea such as by recording a neural response to stimulation. A recipient's T and C levels vary over time as result of tissue degradation (permanent change in levels), or as a result of a short term condition or illness (temporary change).

T and C levels are, generally, stored in an external component of an implantable hearing prosthesis, but may also be stored in an internal component, or within a fully implantable prosthesis with no external components. Because the T and C levels are stored values, an implantable hearing prosthesis, such as cochlear implant 100, may operate as a self-correcting device. That is, the integrity system comprising evaluator 130 and measurement unit 109, may perform diagnostic operations that correct issues with the device. The integrity system may, for example, perform self-correcting by modifying the T and C levels in response to detection of issues, such as increased perilymph impedance. For example, the integrity system may increase stimulation levels, that is, the amount of charge delivered, for stimulation channels which appear to have high perilymph impedance, in an attempt to improve hearing at that stimulation channel. As this is a modification which could potentially provide discomfort to the recipient, evaluator 130 may provide an indication to the recipient of the potential fault and ask for confirmation that the T or C level should be altered. If discomfort or no improvement is registered in response to the change, then the levels can be reset to the original values and the issue passed to a clinic for further analysis.

As mentioned above, the detection of shunt impedances, perilymph impedances and the changes of these impedances over time by evaluator 130 allows automatic detection and reporting of actual or potential fault conditions in the electrode array of the implantable hearing device. Also as noted, these detections may be performed through comparison either to earlier values, other electrode pairs or to threshold levels.

Both the supply voltage tests and the electrode array tests are examples of tests which can be conducted by the integrity system in accordance with embodiments of the present invention. These tests may be performed while the recipient is wearing the prosthesis for daily listening. That is, the tests are real-time tests performed during normal operation of the prosthesis.

Sound coding strategies generally use power-up frames to fill up idle periods, where no, or only low sound, input exists. In embodiments of the present invention, a power-up frame is replaced or supplemented with a measurement frame and can, for example, acquire one measurement point of the impedance matrix. The measurements are performed with sub-threshold stimulation currents and, therefore, the recipient would not "hear" any of the test stimulations. Alternatively, measurement frames could be introduced at controlled intervals into the stimulation frames, for example, every few seconds. Since a measurement frame only lasts a few tenths of micro seconds, equally, the recipient would not notice them. Where the implantable hearing device has a different power source, such as in a fully implantable system where all components are implanted and a battery is used for power, the tests could be run at night, while the implant is not being used for hearing. The integrity system could automatically execute the measurements at regular intervals such as, for example, once a day, week or month.

As mentioned above, the integrity system would be tasked with monitoring the operation of cochlear implant 100, and ensuring that operation is within pre-defined parameters. A further improvement is the automatic modification of the operation of cochlear implant 100. For example, if a shunt, open circuit or short circuit occurs at a particular electrode due to, for example, a deterioration of the insulation around the electrode, these deviations from expectations can be used to automatically deactivate affected electrodes. For example, if the normalized impedance matrix has values outside tolerances, then the integrity system may alter which electrodes are to be used, deactivating electrodes, if required.

Self-Correcting Escalation

An integrity system adapted to perform self-correcting diagnostic operations is sometimes referred to herein as a self-correcting integrity system. Such systems may also be implemented as a staged self-correcting escalation integrity system. In such embodiments, an escalation algorithm as part of the self-correcting integrity system ensures that recipients receive the correct level of care and/or choice in the modification of the function of their medical device.

For example, an escalation algorithm for an implantable hearing device is implemented as follows: (1) receive error indication that operation is not as desired, (2) determine appropriate adjustments based on the error indication, (3) determine whether adjustments to be made require recipient and/or health care provider approval, (4) if recipient and/or health care provider approval required: alert recipient to error condition, (5) if recipient and/or health care provider approval not required: make self-correcting adjustments, (6) alert recipient to action taken due to error condition.

In this manner, the escalation algorithm assesses at what point self-correcting should take place. If the error condition is above a pre-defined threshold or is pre-defined as requiring external approval, the integrity system will report the issue to the recipient or healthcare professional in an identifiable manner. Further analysis of the data can then be carried out in a clinical follow-up session, if necessary, to assess whether any other alterations can be made or whether explanation is required. Depending on the severity of the error condition, integrity system may temporarily deactivate an electrode or make other setting changes pending confirmation from the recipient of healthcare professional that an improvement in hearing due to the changes has occurred. If the integrity system detects issues, but is not able to clearly determine which electrodes are affected, or too many electrodes are affected such that automatic correction would cause a large decrement in performance, the system performs a diagnostic operation that instructs the recipient to visit a healthcare provider. The healthcare provider can perform advanced troubleshooting, such as additional testing using surface potential electrode measurements.

If the integrity system deactivates electrodes after an analysis has been performed, the operation of the implant may be altered based on the new configuration. For example, the sound spectrum would be redistributed to the unaffected electrodes. As such, this is another form of corrective diagnostic operations that adjust the functionality of the implant to compensate for defective electrodes caused by current shunts, open and short circuit electrodes. As such, the recipient's hearing performance would be restored from the effects of these damaged electrodes without requiring a visit to a clinic.

Figure 7:
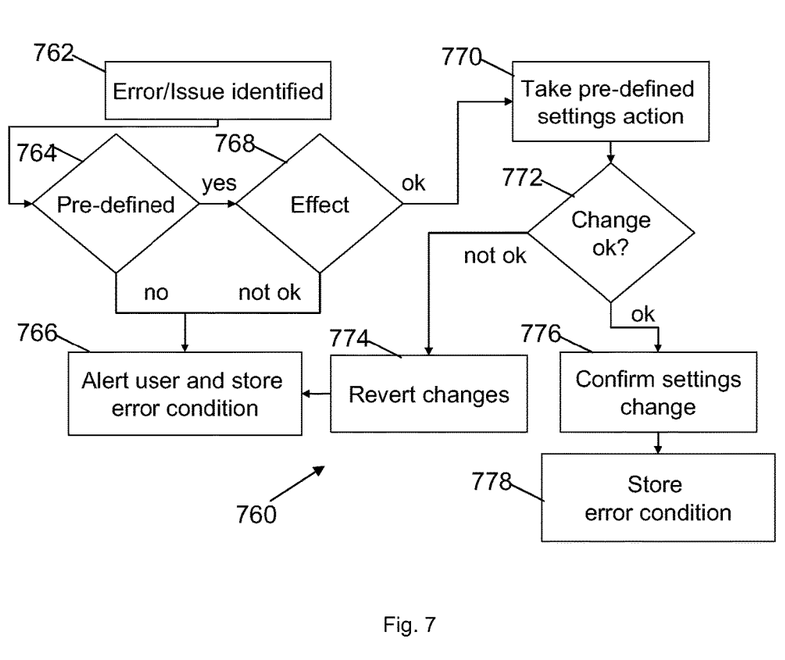
FIG. 7 illustrates a method of self-correcting escalation in an integrity system or method, in accordance with embodiments of the present invention.

FIG. 7 is a flowchart of a self-correcting escalation method 760 that may be implemented in embodiments of the present invention. Method 760 begins at step 762 when an error or issue is identified by, for example, one of the methods described above. At step 764, a check is performed to determine whether the error condition has a pre-defined response. If a pre-defined response is not available, at step 766 the recipient is alerted that an error or issue has been detected and, preferably, stores the error condition for later recall at step 766. The recipient alert can take a number of different forms, as described above, and can have a number of different severity levels. For example, a minor loss in hearing resolution for a cochlear implant may simply alert the recipient to address the issue at the next health care professional appointment. A major error may alert the recipient that immediate attention by a health care professional is required.

If a pre-defined response is defined for the error or issue condition, then a further recipient effect determination is performed at step 768. This step will check what the pre-defined response requires based on the particulars of the error condition. For example, in a cochlear implant, an error condition can require that certain electrodes of the electrode array should no longer be used and the hearing range should be redistributed over the remaining functional electrodes. However, if too many electrodes require to be no longer used, then it would not be possible to redistribute the sound spectrum. In this instant, the effect determination step 768 would not allow the settings of the device to be changed and would revert to step 766 in which the recipient is alerted of the error condition.

If the effect determination step 768 determines that the setting changes are within pre-defined limits, the method continues to step 770 where setting of the implant are adjusted. At this stage a "change ok" step 772 alerts the recipient to the changes and asks to confirm that the settings changes are acceptable. If the settings are not acceptable to the recipient, then a "revert changes" step 774 reapplies the original settings and step 766 of alerting the recipient and storing the error condition is applied. I f the recipient accepts the settings changes, then the method confirms the settings change at step 776 and stores the error condition at step 778 so that a health care professional can be alerted to the error condition and settings change at the next health care professional meeting.

Whereas impact resistance has greatly improved in implantable hearing design, the most fragile component remains the electrode array and associated lead wires. The most frequently observed electrode array faults are open or short circuits or breakdowns of the insulation properties between the electrodes. Faults on the electrode array and associated lead wires can cause a significant decrement in hearing performance for the recipient, especially if undetected due to non-availability or lack of access to respective test methods. Breakdowns in the insulation properties between electrodes can cause a significant redistribution of the stimulation current to other electrodes and by that can reduce speech intelligibility and cause distorted sound quality.

In addition, information on perilymph properties in the cochlea can detect changes caused by, for example, scar tissue growth or ossification. Such information can be useful in the troubleshooting process for recipients. Examples are reports of facial nerve simulation, which are more likely seen with an ossified cochlea.

Having information on the perilymph status at hand allows a more holistic assessment of the case and potentially a better targeted recommendation for mapping changes, which hopefully will alleviate the report. Another example is the absence of Neural Response Telemetry (NRT) recordings, which is often seen with an ossified cochlea. Traditionally, similar information is only available by radiography and often difficult to obtain due to imaging resolution or quality.

The normalization matrix addresses the current need for better differential diagnostics for implantable hearing devices affected by shunting currents in the field. Taking only impedance measurements is less sensitive than the normalization procedure described above.

Implantable hearing prostheses are becoming more common in markets which currently have poorer service levels either due to lower education or poorer accessibility of the service providers. In such markets electrode damage caused by, for example, breaches in the insulation do not get readily detected. As a result, the affected recipients may experience a decreased performance. An implantable hearing prosthesis having an integrated integrity system to evaluate and repair certain issues (self-correcting) allows the recipient to maintain the maximum benefit of the device at all times, even when access to a service provider or clinic is limited.

The invention is not limited to the embodiments illustrated in the drawings but can be varied within the scope of the accompanying claims.

What is claimed is:

1. A method performed at a hearing prosthesis, comprising:
    performing a plurality of bipolar measurements on a plurality of electrodes configurable as bipolar electrode pairs, wherein at least one or more of the electrodes are implanted in a recipient's cochlea;
    determining, based on the bipolar measurements, a bipolar impedance value for each of a plurality of the bipolar electrode pairs;
    performing one or more common ground measurements at each of the plurality of bipolar electrode pairs;
    resolving, using the one or more common ground measurements and a model of the implanted cochlea behavior, each of the bipolar impedance values into a perilymph impedance component and an electrode-tissue impedance component;
    analyzing the perilymph impedance components and the electrode-tissue impedance components; and
    initiating, at the hearing prosthesis, one or more diagnostic operations based on the analysis of the perilymph impedance components and the electrode-tissue impedance components.

2. The method of claim 1, wherein analyzing the perilymph impedance components and the electrode-tissue impedance components, comprises:
    determining, based on the bipolar impedance values, the one or more common ground measurements, and the model of the implanted cochlea behavior, the presence of abnormal current flow between two or more of the implanted electrodes.

3. The method of claim 2, further comprising:
    classifying the degree of the abnormal current flow between the two or more of the implanted electrodes.

4. The method of claim 3, wherein initiating the one or more diagnostic operations, comprises:
    initiating a diagnostic operation based on the degree of the abnormal current flow between the two or more of the implanted electrodes.

5. The method of claim 1, wherein analyzing the perilymph impedance components and the electrode-tissue impedance components, comprises:
    detecting, based on the bipolar impedance values, the one or more common ground measurements, and the model of the implanted cochlea behavior, a change in a behavior of current flow through the perilymph of the cochlea.

6. The method of claim 5, wherein detecting a change in the behavior of current flow through the perilymph of the cochlea comprises:
    detecting a deviation from expected behavior of current flow through the perilymph of the cochlea.

7. The method of claim 5, wherein detecting a change in the behavior of the current flow through the perilymph of the cochlea comprises:
 detecting an increase in the perilymph impedance component of one or more bipolar impedance values.

8. The method of claim 5, wherein detecting a change in the behavior of the current flow through the perilymph of the cochlea comprises:
 detecting a non-linearity between perilymph impedance components associated with two or more bipolar impedance values.

9. The method of claim 5, wherein detecting a change in the behavior of the current flow through the perilymph of the cochlea comprises:
 detecting a larger than expected difference between perilymph impedance components associated with bipolar impedance values determined for successive electrodes.

10. The method of claim 1, wherein analyzing the perilymph impedance components and the electrode-tissue impedance components, comprises:
 detecting, based on the bipolar impedance values, the one or more common ground measurements, and the model of the implanted cochlea behavior, a change in an electrode-tissue impedance component of one or more bipolar impedance values.

11. The method of claim 10, wherein detecting a change in the electrode-tissue impedance component of one or more bipolar impedance values comprises:
 detecting an increase in the electrode-tissue impedance component of the one or more bipolar impedance values.

12. The method of claim 10, wherein detecting a change in the electrode-tissue impedance component of one or more bipolar impedance values comprises:
 detecting a non-linearity in electrode-tissue impedance components associated with two or more bipolar impedance values.

13. The method of claim 10, wherein detecting a change in the electrode-tissue impedance component of the bipolar impedance values comprises:
 detecting a larger than expected difference between electrode-tissue impedance components associated with bipolar impedance values determined for successive electrodes.

14. A method performed at a hearing prosthesis, comprising:
 performing a plurality of bipolar measurements on a plurality of electrodes configurable as bipolar electrode pairs, wherein one or more of the electrodes are implanted in a recipient's cochlea;
 determining, based on the bipolar measurements, a bipolar impedance value for each of a plurality of the bipolar electrode pairs,
 performing one or more common ground measurements at each of the plurality of bipolar electrode pairs;
 detecting, based on the bipolar impedance values, the one or more common ground measurements, and a model of the implanted cochlea behavior, a change in at least one of the behavior of the current flow through perilymph of the cochlea or a change in an electrode impedance of the cochlea;
 initiating, at the hearing prosthesis, at least one diagnostic operation based on the detected change in at least one of the behavior of the current flow through perilymph of the cochlea or a change in an electrode impedance of the cochlea analysis of the perilymph.

15. The method of claim 14, wherein detecting a change in at least one of the behavior of the current flow through the perilymph of the cochlea or in an electrode impedance of the cochlea comprises:
 resolving the bipolar impedance values into perilymph impedance components and electrode-tissue impedance components.

16. The method of claim 15, further comprising:
 determining, based on the bipolar impedance values, the one or more common ground measurements, and the model of the implanted cochlea behavior, the presence of abnormal current flow between two of the implanted electrodes.

17. The method of claim 15, wherein detecting a change in the behavior of the current flow through the perilymph of the cochlea comprises:
 detecting an increase in the perilymph impedance component of one or more bipolar impedance values.

18. The method of claim 15, wherein detecting a change in the behavior of the current flow through the perilymph of the cochlea comprises:
 detecting a non-linearity between perilymph impedance components associated with two or more bipolar impedance values.

19. The method of claim 15, wherein detecting a change in the behavior of the current flow through the perilymph of the cochlea comprises:
 detecting a larger than expected difference between perilymph impedance components associated with bipolar impedance values determined for successive electrodes.

20. The method of claim 15, wherein detecting a change in an electrode impedance of the cochlea comprises:
 detecting an increase in electrode-tissue impedance components of one or more bipolar impedance values.

21. The method of claim 15, wherein detecting a change in an electrode impedance of the cochlea comprises:
 detecting a non-linearity in electrode-tissue impedance components associated with two or more bipolar impedance values.

22. The method of claim 15, wherein detecting a change in an electrode impedance of the cochlea comprises:
 detecting a larger than expected difference between electrode-tissue impedance components associated with bipolar impedance values determined for successive electrodes.

23. The method of claim 14, wherein initiating the at least one diagnostic operation comprises:
 adjusting one or more of settings in the hearing prosthesis, wherein the one or more of settings are selected from the group consisting of: a set of electrodes in use, distribution of the acoustic sound spectrum across the electrodes in use, acoustic threshold levels, maximum comfort level, and power supplied for implant operations.

* * * * *